United States Patent
But (10) Patent No.: US 11,174,562 B2
(45) Date of Patent: Nov. 16, 2021

(54) METHOD AND ELECTROLYTIC CELL FOR THE PRODUCTION OF DETERGENTS AND DISINFECTANTS LIQUIDS

(71) Applicants: Mario Pica, Rome (IT); Igor But, Tallin (EE)

(72) Inventor: Igor But, Tallin (EE)

(73) Assignees: Igor But, Tallin (EE); Mario Pica, Rome (IT)

( * ) Notice: Subject to any disclaimer, the term of this patent is extended or adjusted under 35 U.S.C. 154(b) by 0 days.

(21) Appl. No.: 16/469,999

(22) PCT Filed: Jul. 16, 2017

(86) PCT No.: PCT/IB2017/058029
§ 371 (c)(1),
(2) Date: Jun. 14, 2019

(87) PCT Pub. No.: WO2018/109748
PCT Pub. Date: Jun. 21, 2018

(65) Prior Publication Data
US 2020/0181783 A1    Jun. 11, 2020

(30) Foreign Application Priority Data

Dec. 16, 2016  (IT) .................. 102016000127542
Jun. 27, 2017  (IT) .................. 102017000071890

(51) Int. Cl.
*C25B 9/19*    (2021.01)
*C02F 1/461*   (2006.01)
(Continued)

(52) U.S. Cl.
CPC ............... *C25B 9/19* (2021.01); *C25B 1/46* (2013.01); *C25B 11/02* (2013.01); *C25B 13/02* (2013.01);
(Continued)

(58) Field of Classification Search
None
See application file for complete search history.

(56) References Cited

U.S. PATENT DOCUMENTS 4,374,014 A * 2/1983 Smith .................. C25B 9/08
204/260
4,711,426 A * 12/1987 Bodnar ............. F16L 21/08
251/151

(Continued)

FOREIGN PATENT DOCUMENTS

EP  2253742 A1  11/2010
GB  2264543 A * 9/1993 .............. F16L 19/10
(Continued)

*Primary Examiner* — Harry D Wilkins, III
(74) *Attorney, Agent, or Firm* — Browdy and Neimark, PLLC (57) ABSTRACT

The invention provides an electrolytic cell and, more precisely, an electrolytic cell for the production of disinfecting liquids and detergents, the cell has a cylindrical tubular construction and wherein the cathode and the anode are arranged coaxially one with respect to the other, and wherein the anode has a conical shape. The invention furthermore also provides the operating method of the aforesaid electrolytic cell for the production of the aforementioned disinfectant and detergent liquids.

23 Claims, 5 Drawing Sheets

(51) Int. Cl.
*C25B 1/46* (2006.01)
*C25B 11/02* (2021.01)
*C25B 13/02* (2006.01)

(52) U.S. Cl.
CPC . *C02F 1/46104* (2013.01); *C02F 2201/46115* (2013.01)

(56) References Cited

U.S. PATENT DOCUMENTS

| | | | |
|---|---|---|---|
| 5,635,040 A * | 6/1997 | Bakhir | C25B 9/08 |
| | | | 204/260 |
| 7,374,645 B2 | 5/2008 | Davis | |
| 7,897,023 B2 | 3/2011 | Bakhir | |
| 8,795,483 B2 | 8/2014 | Iltsenko | |
| 2004/0060815 A1 * | 4/2004 | Buckley | C02F 1/4618 |
| | | | 204/230.2 |
| 2007/0272549 A1 * | 11/2007 | Davis | C25B 9/19 |
| | | | 204/260 |
| 2009/0266709 A1 | 10/2009 | Iltsenko | |
| 2012/0168319 A1 | 7/2012 | Iltsenko | |
| 2013/0146473 A1 | 6/2013 | Lambert | |
| 2014/0131217 A1 | 5/2014 | Buschmann | |

FOREIGN PATENT DOCUMENTS

| | | |
|---|---|---|
| GB | 2483555 A | 3/2012 |
| WO | 2005/093129 A1 | 10/2005 |

\* cited by examiner

METHOD AND ELECTROLYTIC CELL FOR THE PRODUCTION OF DETERGENTS AND DISINFECTANTS LIQUIDS

The present invention relates to an electrolytic cell and, more precisely, to an electrolytic cell for the production of disinfectant and detergent liquids which incorporates a conical anode coaxially with the cathode.

The invention also relates to the operating method of the aforesaid electrolytic cell for the production of the aforementioned disinfectant and detergent liquids.

STATE OF THE ART

To date, a number of technologies are already known for the production of electrolytic cells addressed to plants for the production of chemical solutions.

For example, in the field of disinfection and sterilization of water and organic and inorganic liquids already exist coaxial electrochemical cells which starting from an aqueous solution of sodium chloride there can be obtained a production of disinfecting liquids and detergents.

Disinfectant liquids can be used in all applications where it is necessary to disinfect air, organic and/or inorganic liquids, as well as objects. Detergent liquids can be also used as degreasers.

In general, the electrolytic cell it is composed of three coaxial cylindrical bodies:
  an anode, having the largest diameter;
  a cathode, with the smaller diameter; and
  a membrane, which has an intermediate diameter and which it is interposed between the two electrodes above described.

The aforementioned devices are assembled and equipped with a series of mechanical and electrical components that guarantee both the mechanical tightening of the parts, and the pressure sealing of the process fluids, as well as the electrical supply to the electrodes.

The cell must be powered with direct current electricity and with a process fluid consisting of an aqueous sodium chloride solution which hydraulically enters the anode and the intermediate membrane from an inlet line. The sodium chloride molecules contained in the aqueous solution are separated by electrolysis and give rise to the release of chlorine and sodium.

More precisely:
1. Sodium passes through the ceramic membrane and produces the detergent liquid in the hydraulic line between the cathode and the membrane. This line is supplied with water; and
2. Chlorine does not pass through the membrane and remains in solution producing the disinfectant liquid to the corresponding output line.

During operation, the electrodes operate in direct current and produce thermal energy due to the Joule effect, which must be adequately disposed by water or air cooling systems to avoid excessive overheating of components with consequent breakage.

The anode it is subjected to high direct current passage which over time tends to trigger chemical oxidation and etching on the inner surface contacting the process fluid, due to the presence of electric charges which entail the progressive thinning of the thickness of the metal that composes the anode.

To overcome these drawbacks, which entail anode degradation with reduced performance and structural weakening with potential micro-cracks and hydraulic leaks, the inner surface of the anode is covered by a substrate (so-called "coating") composed of a mixture of noble metals which protects the metal of which the anode is made and avoids the occurrence of the phenomena described above.

However, it has been found that the so made electrolytic cells on the current market have a series of critical and intrinsic limits in the structural design of the same cells, which entails severe reliability and performance limits during operation, installation and/or maintenance steps.

For example, U.S. Pat. No. 8,795,483 B2 discloses a coaxial cylindrical electrolytic cell, which has an anode consisting of a metallic cylindrical body where at the ends thereof two plastic heads are connected to, the heads being screwed through threads obtained in the plastic body itself.

This constructive solution has the disadvantage given by the structural limits of the materials in the threading seat. It follows, the formation of cracks in the heads, with consequent hydraulic leaks that compromise the operation of the entire cell.

Moreover, another disadvantage of this constructive arrangement lies in the fact that the hydraulic seal consists of a normal O-ring in a seat formed in the plastic head and compressed by the anode end. Therefore, with such a constructive arrangement the optimal compression of the seal it is not guaranteed with consequent compromise of the seal and leakage of the process liquid, which can trigger a corrosion of the external side of the metal material not protected by the coating.

Moreover, a cylindrical coaxial electrolytic cell it is known from the US patent U.S. Pat. No. 7,374,645 B2, which provides that the coupling between the parts be realized by pass-through penetration of the head inside the anode and interposition of rubber seals.

This constructive arrangement has the disadvantage given by the fact that an optimal seal to the liquid it is not guaranteed, and that damage occurs to the plastic material due to mechanical stress due to fatigue, to the high temperatures, and to the metal corrosion.

In document U.S. Pat. No. 7,897,023B2 a process for producing gaseous electrolyte products such as chlorine and oxygen starting from the electrolyzation of aqueous solutions of alkali metal or alkali metal chlorides it is described, and for use in water purification and disinfection processes and for the electrochemical production of some chemical products. According to this method a coaxial electrolytic cell it is provided, and which has a cell cooling system with an external heat exchanger.

This constructive arrangement shows some disadvantages in terms of additional hydraulic connections required, of construction, and maintenance of the cooling fluid recirculation circuits.

On the other hand, document U.S. Pat. No. 9,340,883B2 discloses an electrolytic method for the production of disinfectants widely used in medicine, biology and ecology, starting from the electrolyzation of an aqueous solution of electrolytes with various concentrations.

This production process and the relevant electrolytic cell have the disadvantage of not guaranteeing sufficient disposal of the generated heat, also due to the low thermal conductivity of the diaphragm, the anode chamber, and the anode itself, with a consequent criticality for the entire electrolytic cell.

Document US20130146473A1 discloses an electrolysis method for producing diluted solutions of sodium hydroxide (NaOH) and diluted solutions of hypochlorous acid (HClO)

with cleaning and sanitizing properties. The method involves the use of an electrolysis coaxial cell equipped with three chambers.

According to this document, the method comprises recirculating an aqueous solution of sodium chloride or potassium chloride into the central chamber of the cylindrical electrolytic cell, and the supplying of softened filtered water into the cathode chamber and into the anode chamber.

This method has several disadvantages as follows:
in electrical terms there is a double electrical resistance determined by the two membranes which makes the electric field applied by the electrolytic cell uneven and non-uniform with an increase in energy consumption and a deterioration in the quality of the electrolysis achieved;
the thermal insulation it is doubled due to the presence of the double diaphragm with worsening of the efficiency in the disposal of the produced heat;
due to the presence of three chambers in the electrolytic cell there is a greater encumbrance of the components and an increase of the necessary hydraulic connections. A further disadvantage is the absence of cell cooling systems.

The object of the present invention it is to solve the aforementioned disadvantages/problems of the state of the art by providing a coaxial electrolytic cell wherein the cathode has a cylindrical shape while the anode has a conical shape. Another object of the present invention is to solve the aforementioned disadvantages/problems of the state of the art by providing a method for the production of aqueous disinfectant and detergent solutions with very low or no saline residue, and by the use of a diaphragm coaxial electrolytic cell which has an electrode liquid cooling system.

BRIEF DESCRIPTION OF THE INVENTION

The present invention provides a coaxial electrolytic cell comprising an anode, a cathode, a membrane, two heads, a closing device, gaskets and screws that can be assembled without the use of tools, and wherein the anode has a conical shape. Once the cell it is powered by direct current electricity, it allows the production of disinfecting and/or detergents liquids starting from an aqueous solution with sodium chloride.

Furthermore, the present invention provides a method for producing aqueous solutions of diluted sodium hydroxide (NaOH) and/or diluted hypochlorous acid (HClO) having disinfectant and detergent properties in an electrolytic cell.

Thus, the present invention provides an electrolytic cell and a production method substantially according to the appended claims.

DETAILED DESCRIPTION OF THE INVENTION

It will now be given a detailed description of two preferred embodiments of the electrolytic cell for the production of disinfecting and detergent liquids which incorporates a conical anode coaxially with the cathode and according to the present invention, given by way of non-limiting example, with reference to the accompanying drawings wherein.

With reference now to the figures, the arrangement and operation of the electrolytic cell according to the present invention will be here illustrated.

Figure 1:
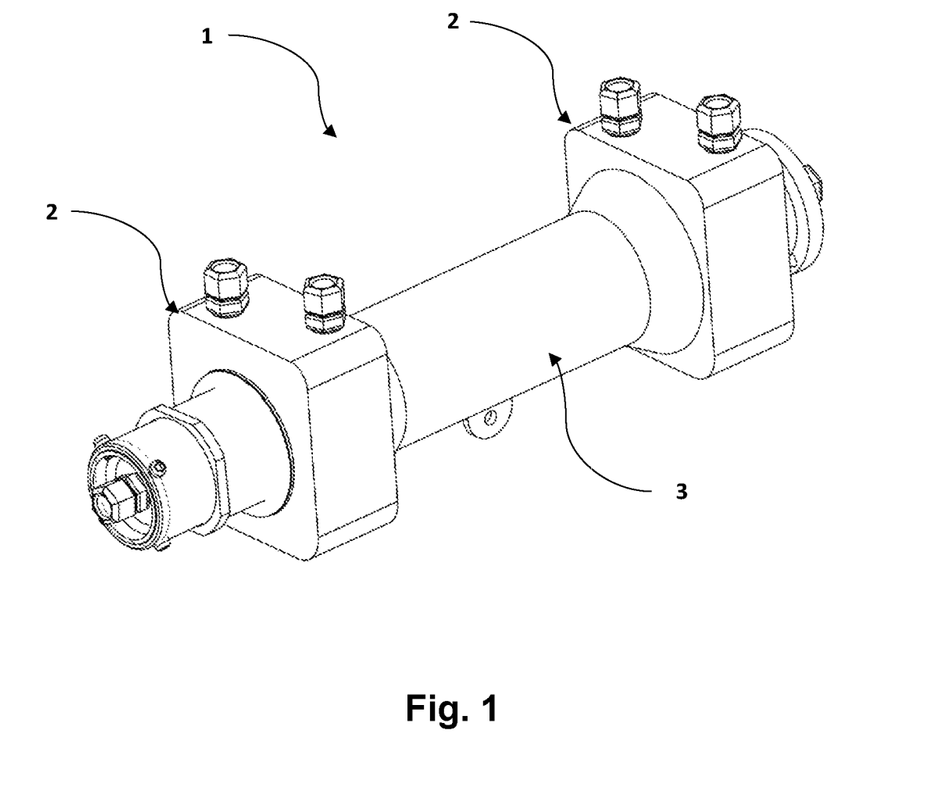
FIG. 1 is a perspective view of the cell of the present invention according to a first embodiment thereof.
Figure 2A:
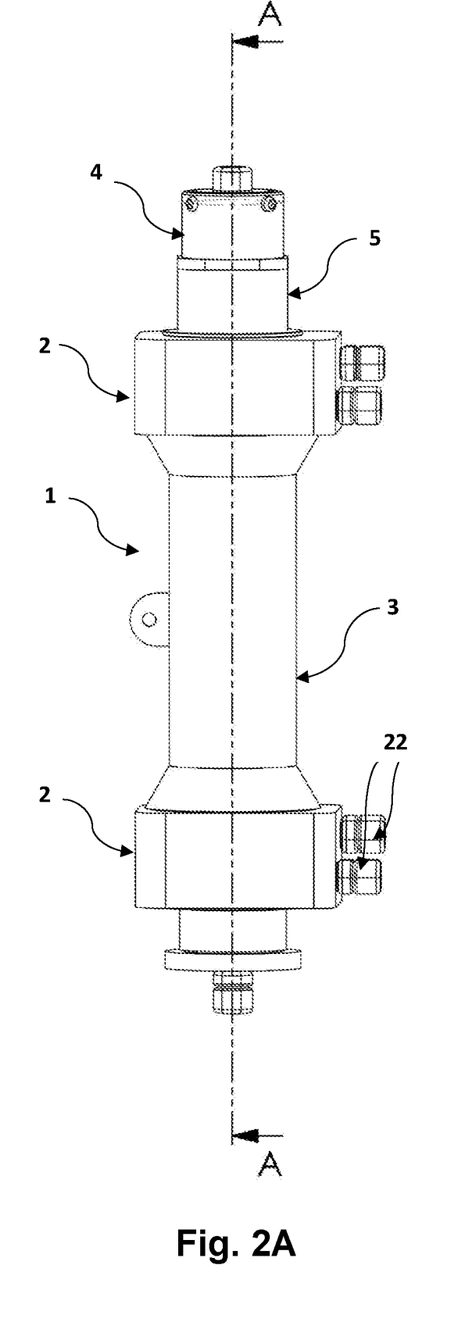
FIG. 2A is an elevation view illustrating the electrolytic cell of FIG. 1.
Figure 2B:
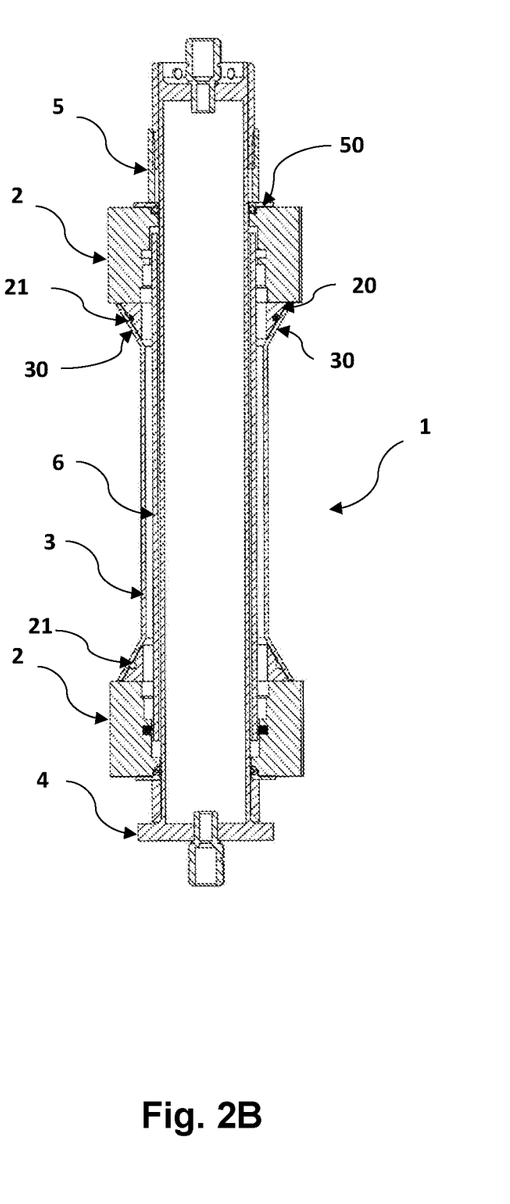
FIG. 2B is a longitudinal sectional view illustrating the cell of FIG. 2A taken along line AA.
Figure 3A:
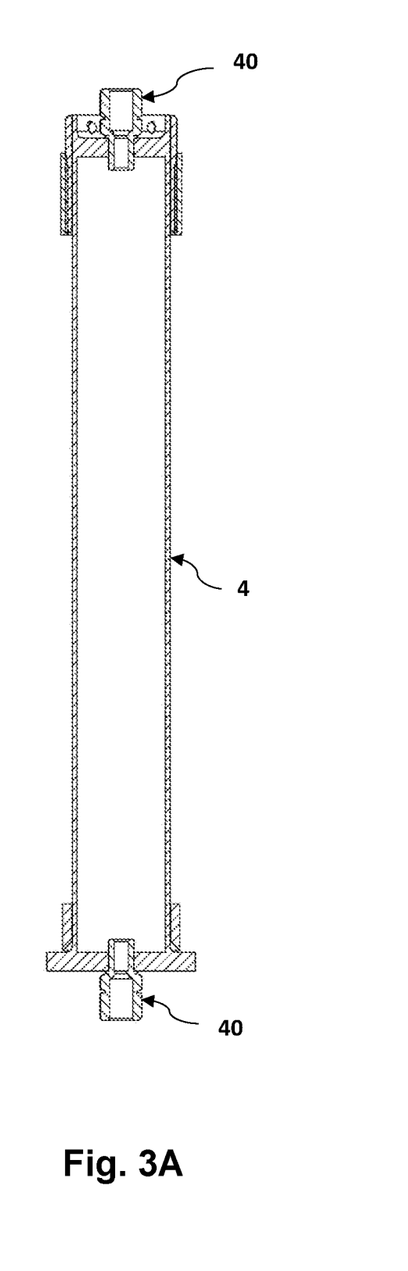
FIG. 3A is a sectional longitudinal view of the cylindrical body of the cathode of the cell of FIG. 1.
Figure 3B:
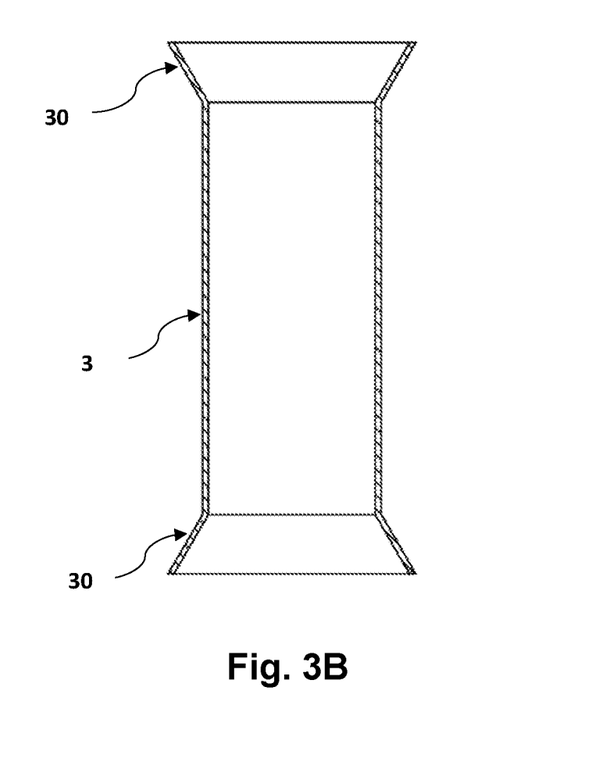
FIG. 3B is a longitudinal sectional view of the anode body of the cell of FIG. 1.

With reference now to FIGS. 1, 2B and 3B, the cell has a substantially cylindrical main body 1 which coaxially arranged comprises a cathode 4, a membrane 6, and an anode 3, and wherein two heads 2 are respectively provided at the end parts thereof.

As evident in FIGS. 2B and 3B, the cell 1 comprises an anode 3 which it is constituted by a tubular member having a conical (tapered) shape. More precisely, the anode 3 has a central cylindrical body whose ends 30 are shaped like a frustoconical section and connected to the central body.

The shape factor and the opening angle of the conical ends 30 has been studied, developed and optimized for avoiding of a series of problems related to the typical geometries of coaxial electrolytic cells.

As shown in FIG. 2B, thanks to the conical shape of the ends 30 of the anode 3, the following technical solutions are implemented:
the head 2 has coupling surfaces 20 and gaskets 21 which are parallel to the ends 30;
the coupling between anode 3 and the heads 2 is obtained by only pressure contact and without threads;
inside the cell 1 there is a double liquid cooling system between anode 3 and the cathode 4 (FIG. 2B) which is connected to an external cooling circuit by means of fittings 22 on each head 2 (the external circuit not being shown in the figures);
the reactor (i.e., the volume where the chemical reaction occurs) has a constant area hydraulic section;
a self-registering/adjusting mounting system it is here provided;
the shaping of the heads 2 allows the mounting thereof according to different orientations; and
the cell 1 it is manually tightened/closed thanks to the presence of a ring nut 5 (FIG. 2B) which engages on a threaded part of said cathode 4, the stepping forward of said nut 5 urges all the components of the cell 1 in an abutting arrangement and contact tightens each of them up to the stop.

Also, as shown in FIGS. 2B and 3B, according to the present invention, the anode 3 it is made of a single piece and without welding. The conical anode 3 it is produced with a production process that allows its manufacture in a single piece, without welding. Moreover, the connection between the two conical ends 30 and the cylindrical part of the anode 3 has no welds.

This technical solution it is fundamental in that it ensures the continuity of the material, as well as the mechanical, electrical, thermal and structural features of the anode.

Furthermore, and as illustrated in FIG. 3A, the cathode 4 of the cell 1 is substantially a watertight piping equipped with fittings 40, within which the cooling fluid flows, and wherein on the external surface thereof the positive electrode of the process it is obtained.

Figure 4A:
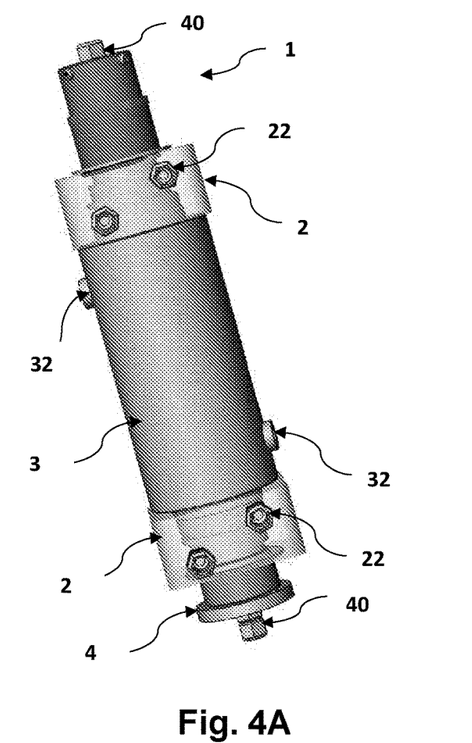
FIGS. 4A to 4C are views illustrating a second embodiment of the cell of the present invention.
Figure 4B:
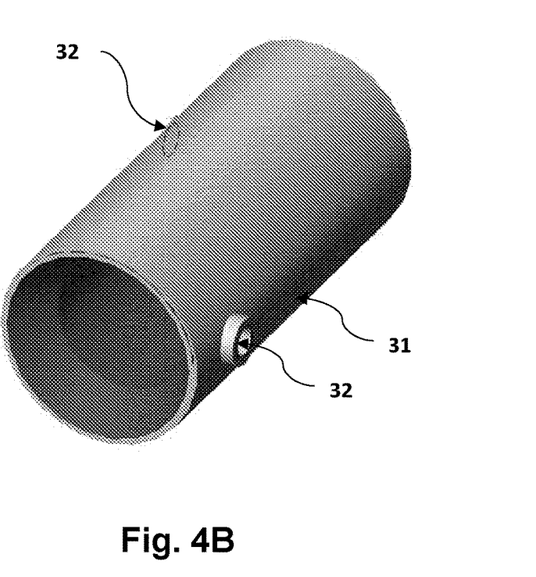
Figure 4C:
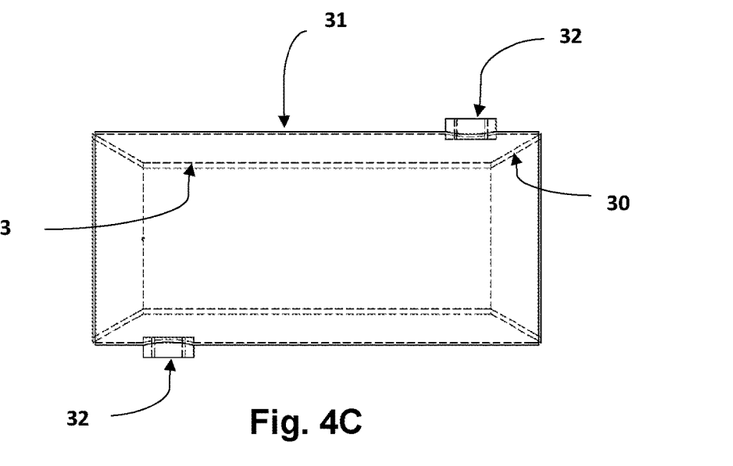

With particular reference now to FIGS. 4A to 4C, there is shown a second embodiment of the electrolytic cell of the present invention wherein a double liquid cooling system of the anode and the cathode it is provided. For the sake of clarity, same parts will have same numbers.

According to this embodiment, the cell anode 3 maintains its conical shape internally and has an outer cylindrical sleeve 31 surrounding outside the anode 3 (FIGS. 4B and 4C), and within which the cooling fluid can circulate through fittings 32 obtained on the sleeve 32 (FIG. 4C).

This constructive solution has allowed the making of a coaxial electrolytic cell with an innovative double liquid cooling system.

More in detail, the double liquid cooling system of the anode 3 and of the cathode 4 allows the increase of the reliability of the system, lowering operating temperatures.

In addition, this construction arrangement allows the increase in the specific production of disinfecting liquids, in the event of an increase in the operating electric currents.

Furthermore, with the cooling sleeve for cooling the anode 3 (FIG. 4C), it is possible to intercept any leak of fluids leaking from the anode 3 due to possible structural cracks.

Further, it is possible to provide onto the outer surface of the cell 1 for any assembly of temperature and conductivity sensors. This solution allows the monitoring of these parameters, therefore in case of leakage of liquid from the anode 3 (which changes the temperature and conductivity of the fluid) there is given the possibility to have an alarm.

Figure 3C:
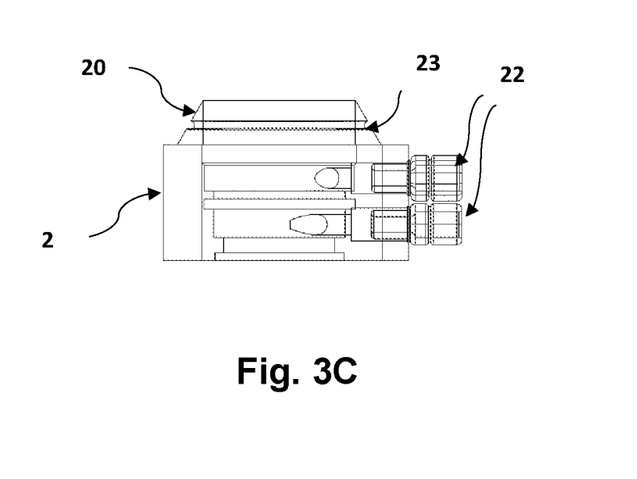
FIG. 3C is a longitudinal sectional view of the joint (header) of the cell of FIG. 1.

With particular reference now to FIGS. 2B and 3C, cell 1 of the present invention has a conical coupling system between the heads 2 and the anode 3.

More precisely, according to the present invention it is provided that the couplings of all the components it is obtained via entirely by pressure contact, and each sealing gasket be compressed between two perfectly parallel surfaces one onto each other.

More precisely and in detail: the head 2 of FIG. 3C it is made of plastic, and in addition to the fluid connection couplings 22, also comprises a seat 23 for the gasket (O-RING) 21 which gasket cooperates with the surface 30 of the conical end of the anode 3 (FIG. 3B), said surface of the conical end 30 being parallel to the plastic surface 20 of the head 2.

Referring now to FIGS. 1, 2A and 2B, the tightening system (by pressure contact) of the components of cell 1 it is shown. As a matter of fact and according to the invention, the components of the cell 1 once assembled are tightened by means of the ring nut 5 and a pressure plate 50, which plate 50 urges and abuts all the parts and components of the cell 1, creating the hydraulic sealing between the anode-head-cathode without the use of further clamping or closing members or dedicated tools.

More precisely, this component closing system made with the ring nut 5 allows a uniform closing pressure to be applied to the components and through the plate 50 and consequently to obtain the hydraulic seal between the anode 3 and the heads 2 and the cathode 4.

Advantageously, this constructive arrangement does not provide for the need to tighten the plastic heads 2 with screws or pins, therefore leading away all risks related to the formation of cracks, or detachments of plastic due to excessive tightening.

Furthermore, thanks to this solution it is possible to obtain any arrangement of the heads 2 and by making them rotate upon the tightening thereof, since being the former perfectly symmetrical they can be rotated by 360° and consequently giving the possibility of a free orientation of the hydraulic connections 22 according to different installation configurations.

Thanks to this configuration it is possible to obtain a closing with a tightening torque that it can be manually modulated by the operator on the ring nut 5 up to the maximum closing torque (equal to about 3 Nm), reachable without the use of any kind of tools.

In addition, the ring nut 5 it is independent from the other components and therefore can be made in any material.

According to another aspect of cell 1 of the present invention, it is provided that the anode 3 incorporates geometries which have been designed to have all surfaces in contact with the process fluids which have linear shapes or with curvature radii within limit values.

This solution allows, during the manufacturing step, an optimal and correct laying of the protective coating due to the absence of sharp angles, edges or cusps. The entire protective layer, correctly laid, works in an optimal manner and without weakening or detaching phenomena, with the advantage of guaranteeing total protection of the anode 3 over time by possible oxidation, corrosion and/or "etching".

According to a further aspect of the cell of the present invention, it is provided that the particular configuration of all the components thereof are absent from problems related to overheating and/or elevated temperatures. In fact, thanks to the geometry of the anode 3, of the heads 2, and of the cathode 4, they are designed and optimized for the optimal removal of the heat generated by the electrochemical process and by Joule effect.

In particular, and as it appears evident from FIG. 2B, the hydraulic section of the cell has a constant area. Along the whole cell 1, in the group consisting of anode 3, heads 2, and cathode 4, the hydraulic section is kept constant to ensure that the flow of the process fluid is maintained in laminar motion, without turbulences or losses, and at constant speed. This solution ensures continuity in the removal of the heat generated by the process.

On the other hand, and as illustrated in FIG. 2B, the section area of the anode 3 at the conical junction points 30 is increased. More precisely and according to the present invention, in proximity to the junction points 30 and at the gaskets 21 for coupling the heads 2 to the anode 3, i.e. where there may be potentially dangerous interstices for the reduction of the speed of the process flow, and therefore of the cooling with the subsequent overheating or steam formation, a detailed designing of the curvature and the geometries has been carried out in order to allow a progressive increase in the diameter of the cones 30, with consequent increase in the distance between the electrodes 3 and 4, which involves a reduction of the Joule effect as well as the formation of heat at the junction points, to guarantee protection of the junction points, and by lowering the voltage and current fields responsible for the development of heat.

According to another aspect of the cell of the present invention, it is foreseen that the same be constructed with components with no welds. More precisely, being the operating process of the cell an electrochemical process type, the absence of welds has multiple values, with reference to:
  mechanical strength thanks to the structural continuity;
  linearity of the surfaces and of the bending curves with
    absence of edges, cusps, or sharp angles, essential for
    the optimization of the laying of the protective coating
    layer (coating);

constant thickness of the anode 3 with no dimensional variations and constant temperature; and uniform transmission of the voltage field towards the process liquid due to the equipotential features of the surface.

Figure 5:
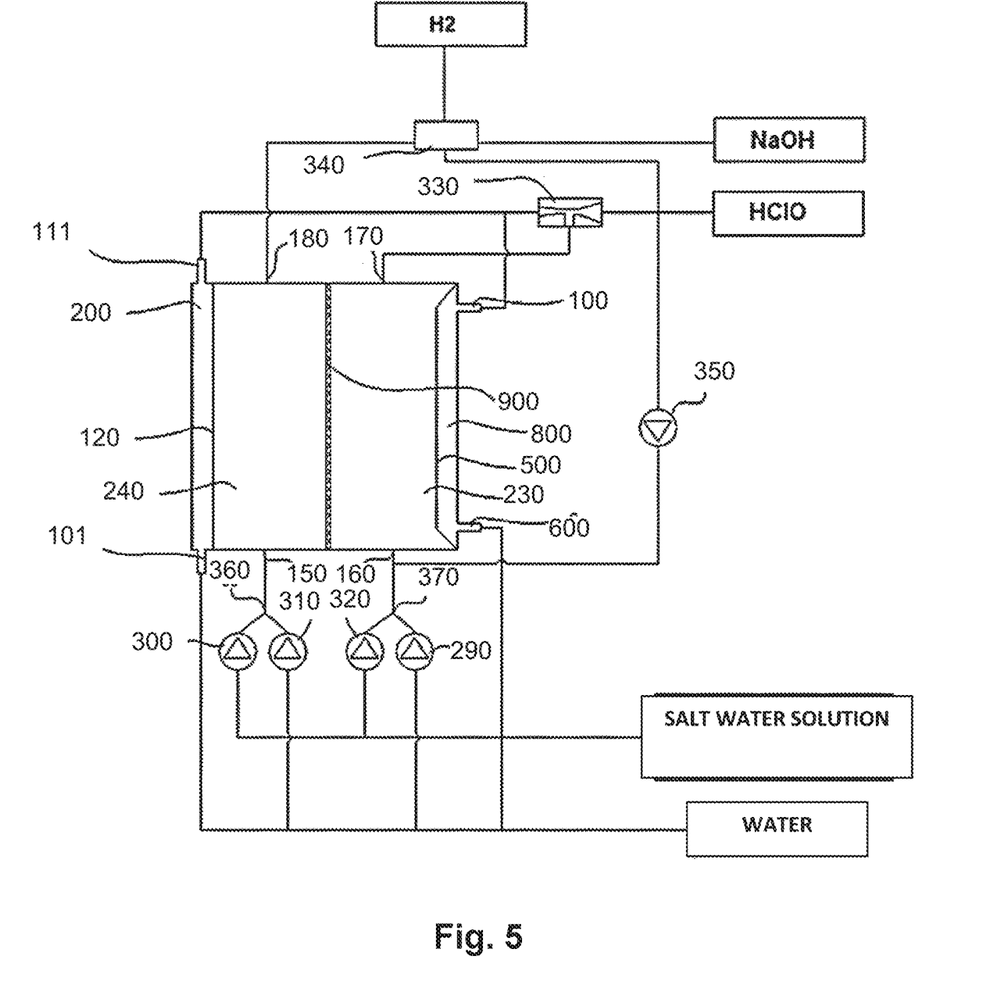
FIG. 5 is a view of the functional scheme relating to the different steps of the production method according to the present invention.

With reference now to FIG. 5, the method of production of a detergent and/or disinfectant solution according to the present invention and through the use of the coaxial electrolytic cell will be here illustrated.

According to the present production method, the increase and the maximization of the electrolysis process performance (REDOX) it is obtained using an electrolytic cell with different operating configurations which allow to obtain disinfectant fluids with different levels of:

hypochlorous acid (HClO);
free active chlorine (FAC—Free Available Chlorine);
ORP (Oxidation-Reduction Potential, REDOX); and
pH The aim of the method it is to produce an aqueous solution of diluted hypochlorous acid (HClO) with low or no residual salinity, henceforth referred to as "anolyte", with high energy efficiency and minimum salt consumption.

According to the present method, at the same time an alkali metal halide is now generated to the cathode from now on called "catholyte" and which contains about 1% to 10% of:

sodium hydroxide (NaOH) (if obtained from a saturated aqueous solution of sodium chloride (NaCl)); or potassium hydroxide (KOH) (if obtained from a saturated aqueous solution of potassium chloride (KCl)).

The catholyte has the advantage of being a cleaning fluid.

Therefore, the method allows to produce anolyte and catholyte with different values of residual salinity, pH and ORP with different solute consumption.

It is known that the process of electrolysis for the generation of a predetermined FAC level requires a known amount of electricity, expressed in Coulomb (C), calculated according to Faraday's Law equation with the following formula:

$$M = A \cdot I \cdot t$$

Wherein
M: mass of substance released in milligrams
A: electrochemical equivalent
I: electric current in Ampere
t: time in seconds In addition, it is well known that electrolysis is not an ideal process and that its efficiency varies from 30% to 60%. In many cases the mass of substance obtained is lower than the amount of theoretical calculation, since there are general inefficiencies related to thermal losses. These losses are in fact related to the conversion into heat, by Joule effect, of part of the electric current used for the electrolytic process and are closely linked to the values of the voltage, the operating current and the electrical resistance of the electrodes and fluids subjected to electrolysis. The heat generated in the cell lowers the efficiency of the process since the increase in temperatures can lead to the emission of substances in gaseous form, such as ClO2, which decrease the contact surface between electrodes and fluids, with a decrease in the efficiency of the cell.

The production method of the present invention provides for the use of a coaxial cell equipped with a liquid cooling system integrated in the anode and in the cathode, thanks to two cooling chambers in contact with the electrodes which allows the disposal and dissipation of the heat generated in the process, keeping the operating temperatures of the fluids and components low and thus preventing excessive thermal expansion of the electrodes.

The coupling of the anode with the plastic heads is conceived with a conical shape and a sealing system with gaskets which, by discharging the stresses and the structural tensions produced by the expansion of the anode outwards, prevent the breaking of the heads.

With particular reference to FIGS. 2A and 2B, a cylindrical electrolytic cell for the production of detergents or disinfectants liquids which implements the production method of the present invention it is illustrated.

The cell has the following characteristics:

A cylindrical cathode 12 (internal electrode) with an internal liquid cooling chamber 2 and hydraulic connections 1 at the ends thereof;

A cylindrical anode 5 (external electrode) with tapered coupling terminals, one external liquid cooling chamber 8, welded pipe, and hydraulic connection fittings;

A coaxial diaphragm 9 with a cylindrical ceramic membrane, with suitable size for the positioning between the electrodes and for the formation of both the anodic chamber 23 and of the cathodic chamber 24;

A protective film for external electrical insulation of the anode;

Electrodes 5 and 12 and diaphragm 9 with coaxial and cylindrical shape factor, which allow coupling with two heads 3 and 4 equipped with hydraulic connection fittings;

A pressure closing system having a threaded ring nut 13 in steel.

According to the method of the present invention, the electrolytic cell has a double liquid cooling system for the production of detergent and disinfecting solutions.

The aqueous solution of diluted sodium hydroxide (catholyte) is more alkaline, has a low or no residual salinity depending on the production procedure used and can be used to clean any surface without rinsing.

The aqueous solution of diluted hypochlorous acid (anolyte) has a low or no residual salinity, depending on the production procedure used, and the available free chlorine content, in addition to the pH, can be regulated in the process. As a result, such aqueous solutions thus obtained can be effectively used for the cleaning and disinfection of surfaces or objects, and through the use of a solution with pH and FAC adjustable according to the application and the various disinfection procedures required.

A detailed non-limiting example of the production method according to the present invention is illustrated in the hydraulic scheme of FIG. 5. More precisely, the production method provides a process which is carried out starting from softened filtered water which is fed at a pressure of approx. 1.0-1.5 bar in the cooling chambers of cathode 200 and anode 800, in the dosing pump of the anode chamber 290, in the cathode dosing pump 310.

The water flows through the cooling chamber 200 of the cathode and the cooling chamber 800 of the anode and, subsequently, it is supplied into an ejector 330, which using the "Venturi" effect it mixes with hypochlorous acid, chlorine, gas, and oxygen coming from the anodic chamber 170 pipe forming the diluted aqueous solution output.

The hydraulic supply of the system it is carried out with four metering pumps which mix the softened water with the saturated aqueous salt solution (KCl or NaCl). In particular, two metering pumps 290 and 320 are provided at the inlet of the anodic chamber 230, and two metering pumps 300 and 310 at the cathode chamber 240, which allow the water to be mixed with the salt saturated solution through the two fittings 360 and 370 "Y" shaped, and with variable and adjustable flow rates to prepare the optimum electrolyte solution for the necessary production method.

Among the various types of metering pumps, the aforementioned metering pumps 290, 300, 310, and 320 are preferably selected as peristaltic pumps, which are preferable due to the wide adjustment/control possibilities they offer. After mixing, the electrolyte flow it is introduced from the fitting 370 to the inlet 160 of the anode chamber and from the fitting 360 to the inlet 150 of the cathode chamber, respectively.

Depending on the operating configurations, the type of desired aqueous solutions at the outlet, and the required FAC concentration, the pumps 290, 300, 310, and 320 can operate at different flow rates, preparing different types of electrolyte inlet solutions that pass through the anodic and/or cathodic chambers of the cell, with a proportion varying from 0.5% to 50% of the total flow. The proportion of water and saturated salt solution can be set according to the generation mode and desired efficiency level.

The direct current it is applied with a voltage of about 5-10 V, with positive polarity connecting to the anode 3 (see FIG. 2A) while with negative polarity being connected to the cathode 4 (see FIG. 2A), so as to induce a current passage between the electrodes, carrying out the electrolysis process and dissociating the electrolyte in the cell, forming the disinfecting and alkaline liquids.

Thus, the disinfectant anolyte is generated from the anode chamber, and the alkaline catholyte is produced by the cathode chamber. The membrane diaphragm interposed between the two electrodes has a porosity that allows the ion exchange between the electrolyte in the anodic and cathodic chambers, allowing the electric current test between the electrodes and prevent mixing of the disinfecting and alkaline liquids that are formed in the cell.

The disinfecting liquid generated in the anode chamber is injected through the outlet 170, into the ejector 330 and mixed with the cooling water coming from the fittings 100 and 110, to form an aqueous disinfectant solution with an FAC variable according to the flow rates set on the metering pumps 290 and 320. The gases formed during the electrolysis process at the anode such as chlorine and oxygen in gaseous form, are removed from the anode chamber 230 by virtue of the vacuum created by the ejector 330 and dissolved in the flow of the cooling water.

On the other hand, the alkaline liquid generated in the cathode chamber 240 with the flow rates set on the metering pumps 300 and 310 is injected, through the outlet 180, into the gas removal device 340 where the gaseous hydrogen is extracted from the process.

From the gas removal device 340 the catholyte obtained can be carried to the discharge or alternatively accumulated in a tank, or recirculated via the metering pump 350 (preferably a variable speed peristaltic pump) and injected through the inlet 160 into the anode chamber 230 to allow the production of an aqueous solution of hypochlorous acid (HClO) diluted with neutral pH.

It should be noted here that according to the production method of the present invention the use of independent and individually adjustable dosing pumps is provided, allowing to obtain various electrochemical processes and/or disinfecting liquids with different characteristics and properties according to the requirements. In fact, according to the present method it is possible to perform a fine regulation of the electrolyte flow rates and concentrations to obtain the electrolysis optimization in the cell. In particular, and depending on the operational needs, using various preset operating configurations that can be stored and managed through a PLC (Programmable Logic Controller) it is possible to produce different predefined types of disinfecting liquids.

According to this method a PLC it is provided, depending on the configuration and the operating mode set, it manages the pumps, the solenoid valves, the sensors and the devices, also using the measurement in feedback of process parameters in order to keep the output product within the set values.

It has to be specified here that according to the present production method, a part of the water inside the anodic chamber ($H_2O$) dissociates into gaseous hydrogen ($H_2$), oxygen ($O_2$) and ozone ($O_3$) according to the following chemical reactions:

in the cathodic chamber in the anodic chamber which give rise, through the combination with sodium (Na) and chlorine (Cl), to an alkaline solution of sodium hydroxide (NaOH) from the cathode chamber, and a disinfectant solution containing a mixture of chlorine monoxide (ClO), chlorates (ClO3) and hypochlorous acid (HClO) from the anode chamber.

According to the circuit diagram of FIG. 5 and as represented by the electrolytic cell of FIGS. 4A to 4C a double cooling system it is provided. Therefore, the minimum flow in the cell which realizes the production method of the present invention and without any risk of breakage due to overheating inside the cell, is equal to a flow rate of 0.20 L/h.

The following TABLE 1 shows the possible operating configurations for obtaining disinfectant liquids with different characteristics by means of the electrolytic cell illustrated herein and which implements the production method of the present invention.

TABLE 1

| | | Operating modes | | | |
|---|---|---|---|---|---|
| | | 1 | 2 | 3 | 4 |
| PUMP [30] | Catodic compartment | OFF | ON | ON | ON |
| PUMP [31] | | ON | ON | OFF | ON |
| PUMP [32] | Anodic compartment | ON | ON | OFF | OFF |
| PUMP [29] | | ON | ON | ON | ON |
| Ph | Anolyte | 7.5 | 5.0 | 4.0 | 3.0 |
| | Catholyte | 11.5 | 11.7 | 12.0 | 12.0 |
| ORP (mV) | Anolyte | 850 | 950 | 1100 | 1150 |
| | Catholyte | −800 | −850 | −800 | −850 |
| Residual salinity (g/L) | Anolyte catholyte | 1.0 0.0 | 1.5 1.5 | 0.0 1.5 | 0.0 2.0 |
| Salt consumption (g/L NaCl) | | 2.5 | 4.0 | 2.5 | 4.0 |

The data in TABLE 1 refer to a configuration with flow rates of pumps 290, 300, 310, and 320 equal to 1.0% with respect to main flow, that is 1 L/h it is injected in a water flow of 100 L/h, with production of the various disinfecting and alkaline liquids at the outlet.

The disinfecting liquids (anolyte) obtained by the production method in the various ways according to the present invention, are suitable for the following uses:

Mode 1: disinfection of poultry farms, dairies, and milk plants,

Mode 2: disinfection of environments very contaminated

Mode 3: disinfection of mains water or drainage

Mode 4: disinfection of heavily contaminated surfaces.

In addition, according to the present method of production it is possible to control the pH, acid/neutral/alkaline, of the aqueous solution of the diluted hypochlorous acid (HClO) by regulating the recirculating pump of alkaline liquids 350.

Advantages

The electrolytic cell of the present invention has the following advantages:

According to a first advantageous aspect of the cell of the present invention, the cracks, cracks and cracks in correspondence are eliminated. of the junction points 30 and the heads 2.

According to a second advantageous aspect of the cell of the present invention, it is possible to avoid damage of the protective coating (coating).

According to a third advantageous aspect of the cell of the present invention, primers and diffusion of "etching" phenomena.

According to a fourth advantageous aspect of the cell of the present invention, the tightening is always optimal during the assembly of the components.

According to a fifth advantageous aspect of the cell of the present invention, installation with hydraulic connections is avoided. aligned.

According to a sixth aspect it goes of the cell of the present invention, the excessive overheating in operation is avoided.

According to a seventh advantageous aspect of the cell of the present invention, with the constructive solutions described above it is possible to disassemble and replace the membrane, the heads 2, the electrodes 3 and 4, and each component of cell 1 with unskilled labor, thanks to the constructive simplicity.

According to an eighth advantageous aspect of the cell of the present invention, the heads 2 are symmetrical and therefore interchangeable for mounting error.

According to a ninth advantageous aspect the cell electrolyte is composed of two electrically insulating clamping heads, which compress two electrodes and a diaphragm, cylindrical and coaxial. The cell is equipped with an integrated cooling of the electrodes, without the need for an external system, which allows the reduction of hydraulic fluid speeds, the containment of the operating temperatures, the maximization of the efficiency of conversion of sodium chloride (NaCl) and the lowering/cancellation of residual salinity.

An advantageous aspect of the method concerns the production, with various flow rates and concentrations, of aqueous solutions of diluted sodium hydroxide (NaOH) and diluted hypochlorous acid (HClO) through the flow of a mixture of water ($H_2O$) and a saturated aqueous solution. of sodium chloride (NaCl) or potassium chloride (KCl) through the anode chamber and/or the cathode chamber of a cylindrical electrolytic cell.

NUMBERS and PARTS IN FIG. 5

[100] Inlet of the cooling chamber of the cathode
[200] cooling chamber of the cathode
[500] cylindrical anode with conical terminals
[600] entry into the anode cooling chamber
[800] anode cooling chamber
[900] porous membrane diaphragm
[101] leaving the anode cooling chamber
[111] output from the cooling chamber of the cathode
[120] cathode
[150] input into the cathode chamber
[160] entry into the anodic chamber
[170] outlet of the anode chamber
[180] output of the cathodic chamber
[230] anode chamber
[240] cathode chamber
[290] anode water metering pump
[300] electrode cathode metering pump
[310] cathode metering pump
[320] anode electrolyte metering pump
[330] "Venturi" ejector
[340] gas removal device
[350] dosing pump for pH correction with alkaline liquid recirculation
[360] "Y" pre-mixing cathodic chamber connection
[370] "Y" pre-mixing anodic chamber connection.

The invention claimed is:

1. An electrolytic cell having a tubular shape with respect to a longitudinal axis and comprising:

in a coaxial arrangement and starting from the center outwards, a cathode, a membrane, an anode, and further comprising two terminal heads arranged at end regions of said cell, said heads comprising hydraulic connections, the two terminal heads comprising a pair of conical shaped sealing surfaces, a closing device which cooperates with said cathode, said membrane, said anode, and said two end heads for mutually tightening and sealing one with respect to the other, and wherein said anode comprises a pair of conical shaped sealing surfaces at end regions of said anode configured to cooperate with said conical shaped sealing surfaces on said terminal heads to obtain sealing of said electrolytic cell, and a sealing member disposed between the pair of conical shaped sealing surfaces at end regions of said anode and said conical shaped sealing surfaces on said terminal heads, wherein said closing device comprises a single ring nut and a flat member both coaxially mounted onto an end threaded region of said cathode, wherein the closing device is configured to cause a mutual hydraulic sealing between the anode and the terminal heads of the cathode of the cell when the pair of conical shaped sealing surfaces at the end regions of said anode fully engage with the pair of conical shaped sealing surfaces on said terminal heads responsive to repeated rotations of said ring nut to tighten all components of said electrolytic cell together.

2. The electrolytic cell having a tubular shape according to claim 1, wherein said anode comprises a cylindrical shaped central body and frustoconical shaped end surfaces integrally connected to said central body.

3. The electrolytic cell having a tubular shape according to claim 2, wherein said the conical shaped sealing surfaces of said terminal heads comprise coupling surfaces.

4. The electrolytic cell having a tubular shape according to claim 3, wherein the functional coupling and sealing between said anode and said heads is obtained by a pressure contact between the pair of conical shaped sealing surfaces at the end regions of said anode and the pair of conical shaped sealing surfaces on said terminal heads.

5. The electrolytic cell having tubular shape according to claim 3, wherein said cathode comprises a tubular body having a hydraulic seal, wherein an inside of the tubular body is configured to receive a cooling fluid flowing from one end to the opposite end of said tubular body and through connecting fittings said fittings being integral with said cathode tubular body.

6. The electrolytic cell having tubular shape according to claim 3, further comprising an outer cylindrical sleeve coaxially mounted onto an outer surface of said anode, wherein a cooling fluid flows between said anode and said sleeve through fittings integrally made onto said sleeve.

7. The electrolytic cell having tubular shape according to claim 3, wherein said heads have a symmetrical shape and are configured to rotate 360° with respect to a longitudinal axis of said cell wherein the rotation of said heads results in free orientation of said hydraulic connections.

8. The electrolytic cell having a tubular shape according to claim 2, wherein the functional coupling and sealing between said anode and said heads is obtained by a pressure contact between the pair of conical shaped sealing surfaces at the end regions of said anode and the pair of conical shaped sealing surfaces on said terminal heads.

9. The electrolytic cell having tubular shape according to claim 2, wherein said cathode comprises a tubular body having a hydraulic seal, wherein an inside of the tubular body is configured to receive a cooling fluid flowing from one end to the opposite end of said tubular body and through connecting fittings said fittings being integral with said cathode tubular body.

10. The electrolytic cell having tubular shape according to claim 2, further comprising an outer cylindrical sleeve coaxially mounted onto an outer surface of said anode, the arrangement being such that between said anode and said sleeve a cooling fluid flows between said anode and said sleeve through fittings integrally made onto said sleeve.

11. The electrolytic cell having tubular shape according to claim 2, wherein said heads have a symmetrical shape and are configured to rotate 360° with respect to a longitudinal axis of said cell, wherein the rotation of said heads results in free orientation of said hydraulic connections.

12. The electrolytic cell having a tubular shape according to claim 1, wherein the functional coupling and sealing between said anode and said heads is obtained by a pressure contact between the pair of conical shaped sealing surfaces at the end regions of said anode and the pair of conical shaped sealing surfaces on said terminal heads.

13. The electrolytic cell having tubular shape according to claim 12, wherein said cathode comprises a tubular body having a hydraulic seal, wherein an inside of the tubular body is configured to receive a cooling fluid flowing from one end to the opposite end of the tubular body and through connecting fittings said fittings being integral with said cathode tubular body.

14. The electrolytic cell having tubular shape according to claim 12, further comprising an outer cylindrical sleeve coaxially mounted onto the outer surface of said anode, wherein a cooling fluid flows between said anode and said sleeve through fittings integrally made onto said sleeve.

15. The electrolytic cell having tubular shape according to claim 12, wherein said heads have a symmetrical shape and are configured to rotate 360° with respect to a longitudinal axis of said cell wherein the rotation of said heads results in free orientation of said hydraulic connections.

16. The electrolytic cell having tubular shape according to claim 1, wherein said cathode comprises a tubular body having a hydraulic seal, wherein an inside of the tubular body is configured to receive a cooling fluid flowing from one end to the opposite end of said tubular body and through connecting fittings, said fittings being integral with said cathode tubular body.

17. The electrolytic cell having tubular shape according to claim 16, further comprising an outer cylindrical sleeve coaxially mounted onto the outer surface of said anode, wherein a cooling fluid flows between said anode and said sleeve through fittings integrally made onto said sleeve.

18. The electrolytic cell having tubular shape according to claim 16, wherein said heads have a symmetrical shape and are configured to rotate 360° with respect to a longitudinal axis of said cell wherein the rotation of said heads results in free orientation of said hydraulic connections.

19. The electrolytic cell having tubular shape according to claim 1, further comprising an outer cylindrical sleeve coaxially mounted onto an outer surface of said anode, wherein a cooling fluid flows between said anode and said sleeve through fittings integrally made onto said sleeve.

20. The electrolytic cell having tubular shape according to claim 19, wherein said heads have a symmetrical shape and are configured to rotate 360° with respect to a longitudinal axis of said cell wherein the rotation of said heads results in free orientation of said hydraulic connections.

21. The electrolytic cell having tubular shape according to claim 1, wherein said heads have a symmetrical shape and are configured to rotate 360° with respect to a longitudinal axis of said cell, wherein the rotation of said heads results in free orientation of said hydraulic connections.

22. A method for the functioning of an electrolytic cell having a tubular shape with respect to a longitudinal axis and comprising in a coaxial arrangement and starting from the center outwards: a cathode, a membrane, an anode, and further comprising two end heads arranged at end regions of said cell, said heads comprising hydraulic connections, a closing device which cooperates with said cathode, said membrane, said anode, and said two end heads for a mutual tightening and sealing of one with respect to the other, and wherein said anode comprises conical shaped surfaces adapted to cooperate with respective interface surfaces of said terminal heads to obtain the sealing of the whole electrolytic cell, wherein said closing device comprises a ring nut and a flat member both coaxially mounted onto a threaded part of said cathode, the method comprising creating a hydraulic sealing between the anode, the two end heads, and the cathode of said electrolytic cell by a manual operation by rotating said ring nut without use of any tool.

23. The method for the functioning of an electrolytic cell having tubular shape according to claim 22, wherein the hydraulic cross section of said electrolytic cell is constant along the whole length of said electrolytic cell, and wherein a process fluid stream passing through said length of said electrolytic cell is maintained at a constant speed.

\* \* \* \* \*